United States Patent [19]
Kiefer

[11] Patent Number: 5,558,742
[45] Date of Patent: Sep. 24, 1996

[54] PROCESS FOR ANALYZING NUTRITIONAL CONTENT OF A COMPOSITION OF FOOD TO PRODUCE A CALCULATED PRINTED REPRESENTATION

[76] Inventor: Helen C. Kiefer, 407 N. Maple Ave., Oak Park, Ill. 60302

[21] Appl. No.: 236,741

[22] Filed: Apr. 28, 1994

[51] Int. Cl.⁶ ..................................................... B32B 3/00
[52] U.S. Cl. .................... 156/244.16; 156/257; 156/453; 156/455; 434/113; 434/114; 29/525
[58] Field of Search ............................. 156/244.16, 257, 156/DIG. 2, DIG. 4, DIG. 18, 453, 455; 400/84, 122, 124; 434/114, 113; 29/525

[56] References Cited

U.S. PATENT DOCUMENTS 4,127,190  11/1978  Sunnen ................................ 206/535
4,488,828  12/1984  Ohtsuki .................................. 400/82
5,152,690  10/1992  Todd ..................................... 434/113
5,336,458   8/1994  Hutchinson et al. .................. 264/220

*Primary Examiner*—Patrick J. Ryan
*Assistant Examiner*—M. Dixon
*Attorney, Agent, or Firm*—Peter K. Trzyna; Baker & McKenzie

[57] ABSTRACT

A process for producing pictorial labels representing content of a composition of food, the process including the following steps: obtaining nutritional data for a composition of food, the nutritional data representing a quantity of a nutrient in the composition; defining a pictorial image representing a standard for daily human consumption of the nutrient; defining an area representing the quantity; and printing a label having the pictorial image and the respective area, to form a pictorial comparison of the quantity of the nutrient in the composition with the standard.

9 Claims, 2 Drawing Sheets

FIG. 9

PROCESS FOR ANALYZING NUTRITIONAL CONTENT OF A COMPOSITION OF FOOD TO PRODUCE A CALCULATED PRINTED REPRESENTATION

I. FIELD OF THE INVENTION

The present invention generally pertains to chemical, manufacturing, and printing processes. More particularly, the invention involves analyzing a composition of food to quantify nutrients therein, and manufacturing/printing a label to pictorially communicate the quantified nutritional information with respect to a standard. In one embodiment, the pictorial image is embossed or textured for sensing by visually impaired people.

II. BACKGROUND OF THE INVENTION

Visual images have been associated with food for some time, probably first appearing on the walls of the cave men. Many sketches, drawings, and single "symbolizations," such as that of a grain of wheat, have been associated with food.

One symbol that has been used in the United States in connection with food is a "food pyramid," which was proposed by the United States Department of Agriculture ("USDA") during the 1980's. In the food pyramid, the width of each horizontal slice through the pyramid represents food groups in an overall human diet.

Use of the food pyramid has been limited by the purpose for which it was intended. For example, the food pyramid is not known to have appeared on specific foods or compositions of food (or labels therefor), nor is the symbol particularly suitable for such use, because it pertains to an overall diet rather than to a specific food or a food composition. Selected nutrient information is neither particularized nor quantified. Moreover, the food pyramid does not represent nutrients in quantities normalized to, say, a recommended daily amount.

Instead, the food pyramid was intended for use in generally informing people of the kinds of food that should be included in their overall diets. Therefore, the symbol was not intended to communicate amounts of key nutrients in a specific food composition that is boxed, canned, frozen, or packaged. Nor does the symbol communicate these amounts with respect to a recipe or a restaurant menu item.

For such purposes, instead of using symbols, nutritional quantities have typically been communicated via tables of mathematical quantities or measurements. And until recently, this form of communication has not even been standardized in the United States. Thus, nutrients were displayed in whatever listing the seller felt comfortable displaying, and in whatever format the seller deemed convenient.

This approach could be manipulated to convey misleading information. For example, nutrient values could be normalized to the total weight of the food. Thus, a particular food containing 90% water could be listed as "90% Fat Free," even if the only ingredient other than water is pure fat. Indeed, labeling had so much potential for such manipulation in the recent past that the term "label abuse" had been coined: "Regulators have targeted three major areas of label abuse: deceptive definitions, hazy health claims, and slippery serving sizes." (*Time*, p. 52, Jul. 15, 1991.)

In a broader view of nutritional labeling, understanding the contents of what one eats is a concern of no small dimension. To this end, there has been a long history in this country of official attempts to develop a national nutrition policy. In principle, it was thought that this policy should make nutritional recommendations (based on the results of dietary research) and that the policy should unify nutritional labeling regulations to make them as honest, fair, and understandable as possible. But implementing a national nutritional policy has not been easy, as summarized in the following excerpt from a book authored by the inventor herein.

> Since the 1940's-when standards for enriching grain products and margarine were established, and the school lunch program commenced-the United States has been attempting to develop a national nutritional policy. By the end of the 1960's, the first U.S. nutritional status study was showing results and the White House Conference on Food, Nutrition, and Health met.
>
> Following the release of the somewhat controversial Dietary Goals for the United States by the Senate Select Committee on Nutrition and Human Needs in December 1977, numerous other scientific and federal groups have issued their own nutritional positions. These groups include the National Research Council-National Academy of Sciences (NAS), the Surgeon General, the U.S. Department of Agriculture (USDA), the Food and Drug Administration (FDA), the Department of Health and Human Services (DHHS, formerly the Department of Health, Education and Welfare), and the Federal Trade Commission (FTC).
>
> In February 1980, the USDA and the DHHS developed their guidelines, "Nutrition and Your Health, Dietary Guidelines for Americans." Although all officials involved in preparing the Dietary Guidelines stressed that these guidelines represented a consensus among government scientists on the current state of nutritional knowledge, other agencies—most notably, the Food and Nutrition Board of the National Research Council—voiced their concern that consensus in the interpretation of scientific facts may not be appropriate for the public decision-making process.

H. C. Kiefer, I. Scarpa, and R. Tatum, *Source Book On Nutrition*, 3rd. ed., Sec. 1, Marquis Academic Media (Div. Marquis Who's Who Publishers), 1981.

The head of the Department of Health and Human Services called food labeling a "Tower of Babel" because no single agency or law regulated food labeling: the FDA regulated part, the Department of Agriculture regulated part, and the Federal Trade Commission regulated the advertising and labeling of foods and nutrients per se, though individual staten could also make nutrition and labeling laws.

Most of these diverse labeling regulations were finally consolidated and gaps were filled by the Nutrition Labeling and Education Act of 1990. The new law requires, among other things, that food labels disclose the following:

(1) the total number of calories
  (i) derived from any source, and
  (ii) derived from the total fat, in each serving size or other unit of measure of the food, (2) the amount of the following nutrients: total fat, saturated fat, cholesterol, sodium, total carbohydrates, dietary fiber, and total protein contained in each serving size or other unit of measure; and (3) any vitamin, mineral, or other nutrient required to be placed on the label and labeling of food.

After the bill was signed into law, the same head of the Department of Health and Human Services was quoted as saying that "The Tower of Babel in food labeling has finally come down . . . " (*Time*, p. 23, Dec. 14, 1992).

By May 1994, the food industry will have to comply with the requirements of this law. Certain key nutrient information must (by May 1994) appear on all produce bins, meat counters, and the labels of boxed, canned, frozen, etc. food products. And the data must be displayed in such terms as calories, grams, milligrams, and percents—notions that are not immediately easy to visualize. Previously, so far as is known, the conventional approach of providing tables of data has been pursued. A representative post-1992 label is quoted below showing how a label for a food composition can communicate nutrient information so as to comply with the new "Nutritional Labelling and Education Act."

Sample Label

Standardized label information showing number of calories, grams of fat and amounts of other nutrients will be on the labels of all packaged products. Values for a sample diet of both 2,000 and 2,500 calories a day will also be on the label.

Nutritional Information
Nutrition Facts
Serving Size ½ cup (114 g)
Servings Per Container 4
Amount per serving
Calories 260; Calories from fat 120

|  | % Daily Value* |
|---|---|
| Total Fat 13 g | 20% |
| Saturated Fat 5 g | 25% |
| Cholesterol 30 mg | 10% |
| Sodium 660 mg | 28% |
| Total Carbohydrate 31 g | 11% |
| Sugars 5 g |  |
| Dietary Fiber 0 g | 0% |
| Protein 5 g |  |

Vitamin A 4%-Vitamin C2%-Calcium 15%
*Percents (%) of a Daily Value are based on a 2,000 calorie diet. Your Daily Values may vary higher or lower depending on your calorie needs:
Recommended Daily Amounts

| Nutrient |  | 2,000 Calories | 2,500 Calories |
|---|---|---|---|
| Total Fat | Less Than | 65 g | 80 g |
| Sat Fat | Less Than | 20 g | 25 g |
| Cholesterol | Less Than | 300 mg | 300 mg |
| Sodium | Less Than | 2,400 mg | 2,400 mg |
| Total Carbohydrate |  | 300 g | 375 g |
| Fiber |  | 25 g | 30 g |

Conversion Chart
1 g Fat=9 calories
1 g Carbohydrates=4 calories
1 g protein=4 calories While extremely valuable in terms of nutritional information, such tables may be difficult for the average consumer to easily understand—quantities expressed as multiple rows of numbers can be daunting, particularly for those who are visually impaired. Thus consumers, who may be unaware of what is good or bad for them, or how much is good or bad for them, may reap limited benefits from the otherwise rather promising new nutritional law. Accordingly, Patrick Boyle, president of the American Meat Institute, supported labeling but called the required label a "morass of numbers . . . neither suitable nor relevant for most Americans." *Washington Times*, p. 1, Dec. 12, 1992.

III. SUMMARY OF THE INVENTION

The present invention is intended to have utility in overcoming such limitations as those described above, and as is more particularly indicated in the following representative objects of the invention.

It is an object of the present invention to provide a method for making a symbolic label for food or a composition of foods.

It is a further object of the present invention to provide a method for making such a label to symbolically communicate empirically-derived nutritional content(s).

It is an additional object of the present invention to provide a method for making such a label that is standardizable to suggested minimum/maximum daily allowances.

It is another object of the present invention to provide a method for making such a label that efficiently communicates such nutritional information.

It is yet another object of the present invention to provide a method for making such a label that is readily adaptable to different kinds of food.

It is yet another object of the present invention to provide a method for making such a label for use including direct application on produce or bins of produce, on meat counters, on packaged food including canned, boxed, frozen, or any other processed foods, on menus for items listed thereon, and in association with recipes, etc.

It is still another object of the present invention to provide a method for making a series of the aforementioned labels to communicate symbolically respective quantities of nutrients in a food or composition of foods.

These and other objects, which are apparent from the detailed description of the invention and other sections provided herein, are accomplished by a method for labeling food or a composition of food. The process includes: A process for making pictorial labels representing content of a composition of food, the process comprising the steps of: obtaining nutritional data for a composition of food, the nutritional data representing an amount of a nutrient in the composition; defining a pictorial image representing a quantitative standard for daily human consumption of the nutrient; defining an area representing said amount of the nutrient in the composition and proportionate to said quantitative standard; and printing a label having said pictorial image and said area to form a pictorial comparison of the amount of the nutrient in the composition with the standard.

As used herein, the term "label" is not limited to printing that is adhered to an article. Rather, the term is used in the sense of labeling as the term is used in the Nutritional Labeling law, for example, written, printed, textured or embossed matter accompanying an article in any way so as to impart information. Accordingly, a nutritional label includes a printing of contents on a box of cereal.

The process can also include using a series of images showing respective sums for respective nutrients. Thus, the process of the present invention permits a symbolic representation of the information to facilitate easy visualization and understanding of nutritional data. For those who are visually impaired, the pictorial image can have a tactile element, for example, by embossing or by producing a texture with the ink or the print used to define the image.

V. DETAILED DESCRIPTION OF A PREFERRED EMBODIMENT OF THE INVENTION

A composition of food can include a single food or a mixture of foods. A composition of food can be unprocessed, or it can be processed, for example, by being canned, bottled, boxed, or frozen products. Additionally, a composition can be indicated in a recipe or a menu.

The present invention is intended to provide nutritional information in a way suitable to each of these circumstances. The present invention is also intended to meet the detailed requirements of existing labeling laws—all by representing the key nutrients in pictorial form and in a standardized manner.

Figure 1:
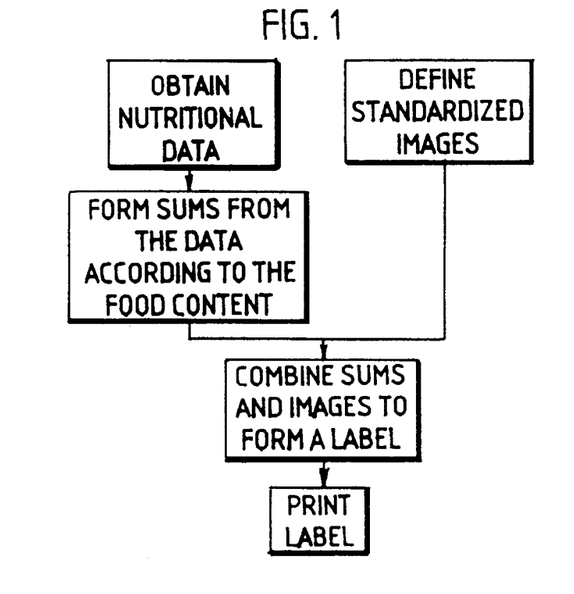
FIG. 1 is a flow chart of the process of the present invention.

As shown in FIG. 1, the process of the present invention can be viewed as having four basic steps, though shortcuts, equivalents, and embellishments exist. The process includes the step of obtaining nutritional data representing a respective quantity of calories and/or at least one nutrient in a food composition. For example, a nutrient of interest might be sodium. Alternatively, or in addition, the same step can be performed to identify calories and the saturated/unsaturated fat associated therewith.

Rather than analyze the composition directly, it is often more efficient to analyze the ingredients before they are combined to form the composition. Then, each quantity for each nutrient of interest is combined to form respective sums for each item of interest in the composition.

Figure 3A:
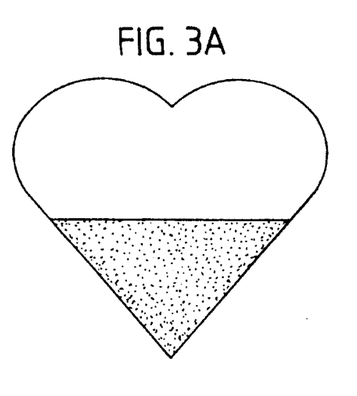
FIGS. 3A and 3B represent symbolic nutrient labels for cholesterol (which include the type of shading that can be used to depict how much cholesterol is present relative to the recommended daily limit).
Figure 3B:
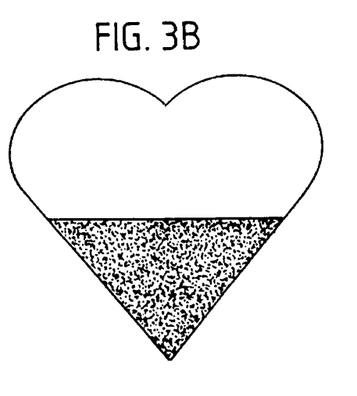

Then, at least one, but preferably a series of, pictorial images are defined such that each image communicates a standard, such as a daily recommended amount of a selected nutrient for consumption by an adult. One of the aforementioned sums is then depicted in combination with the respective one of the images in manufacturing a label or the equivalent. The label provides a pictorial (not alphanumeric) illustration of the sum in comparison with the daily recommended amount for the nutrient (as can be seen from the shading in FIG. 3 for cholesterol).

The pictorial images can be representative of "food values." A "food value" refers to the actual substance that makes up human tissues. These are proteins, carbohydrates, and fat, each of which supplies calories to meet human energy needs, and each of which can be represented as nutrients.

The printing process may emboss the image and area or produce them with a textured ink or the like. The texture or embossing can then also be sensed by the touch of a person who is visually impaired to understand efficiently the nutritional content of the food composition.

These steps are detailed below.

A. Obtaining Nutrient Data

Any nutrient in any food composition can be identified and quantified by known chemical methods. For example, oily substances or fat-soluble vitamins can be quantified by high performance liquid chromatography; amino acid analyzers can be used to quantify protein and amino acid content in food, as well as the "quality" of the protein—i.e., how closely the protein matches that of human tissues; complex carbohydrates and sugars can be analyzed by gas-liquid chromatography; flame atomic absorption spectrometry can be used to determine the mineral content of a food; "bench" colorimetric and gravimetric chemical assays can be used to determine fiber, iodine, caffeine, and other miscellaneous substances as well as to verify the results for all nutrients obtained by the instrumental analyses outlined above.

For the best approaches of the moment, one should consult up-to-date technical literature, but a representative selection of articles organized by nutrient(s) is (are) included by reference as follows.

1. Sodium (and Other Minerals)

The quantity of minerals, including sodium content, in food can be determined by atomic absorption spectroscopy. See, for example, the following references:

Appledorf, H. and L. S. Kelly, "Proximate and Mineral Content of Fast Foods," *J. Am. Diet Assoc.*, 74(1):35–40, 1978, (Ca, P, Na, K, Mg, Fe, Zn, Mn, Cu); and Zook, E. G., F. E. Greene and E. R. Morris, "Nutrient Composition of Selected Wheats and Wheat Products, VI. Distribution of Manganese, Copper, Nickel, Zinc, Magnesium, Lead, Tin, Cadmium, Chromium, and Selenium as Determined by Atomic Absorption Spectroscopy and Colorimetry," *Cereal Chem.*, 47:720–731, 1970.

2. Cholesterol

The quantity of cholesterol in food can be determined by various forms of chromatography. See, for example, the following reference:

Feeley, R. M., P. E. Criner and B. K. Watt, "Cholesterol Content of Foods," *J. Am. Diet Assoc.*, 61:134–149, 1972.

3. Fat

The quantity of fats, fatty substances, and fat soluble vitamins in food can be determined by various forms of chromatography. See, for example, the following references:

Brignoli, C. A., J. E. Kinsella, and J. L. Weihrauch, "Comprehensive Evaluation of Fatty Acids in Foods, V. Unhydrogenated Fats and Oils, " *J. Am. Diet Assoc.*, 68:224–229, 1976;

Exler, J. and J. L. Weihrauch, "Comprehensive Evaluation of Fatty Acids in Foods, XXII," *J. Am Diet. Assoc.*, 71(5):518–521, 1977;

Fristrom, G. A., B. C. Stewart, J. L. Weihrauch and L. P. Posati, "Comprehensive Evaluation of Fatty Acids in Foods, IV. Nuts, Peanuts, and Soups," *J. Am. Diet Assoc.*, 67:351–355, 1975;

Ostwald, R., "Fatty Acids in Eleven Brands of Margarine," *J. Am. Diet. Assoc.*, 39(4):313–316, 1961;

Posati, L. P., J. E. Kinsella and B. K. Watt, "Comprehensive Evaluation of Fatty Acids in Foods, I. Dairy Products," *J. Am. Diet. Assoc.*, 66:482–487, 1975;

Posati, L. P., J. E. Kinsella and B. K. Watt, "Comprehensive Evaluation of Fatty Acids in Foods, III. Eggs and Egg Products," *J. Am. Diet. Assoc.*, 67:111–115, 1975;

Sheppard, A. J., J. L. Iverson and J. L. Weihrauch, "Composition of Selected Dietary Fats, Oils, Margarine, and Butter," Handbook of Lipid Research, vol 1, edited by A. Kuksis, Plenum, New York, 1973;

Parsons, J. G., P. G. Leeney and S. Patton, "Identification and Quantitative Analysis of Phospholipids in Cocoa Beans," *J. Food Sci.*, 34(6):497–499, 1969;

Saucerman, J. R., C. E. Winstead and T. M. Jones, "Quantitative Gas Chromatographic Headspace Determination of Choline in Adult and Infant Formula Products," *J. Assoc. Anal. Chem.*, 67(5):982–985, 1984;

Bentley, R., "A Fresh Look at Lamb," *J. New Zealand Diet. Assoc.*, 40:81–88, 1986. (proximates, 10 vitamins, 9 minerals, amino acids, fatty acids);

Paul, A. A., and D. A. T. Southgate, "A Study on the Composition of Retail Meat: Dissection into Lean, Separable Fat and Inedible Portion," *J. Hum. Nutr.*, 31:259–272, 1977;

Sertl, D. C. and B. E. Molitor, "Liquid Chromatographic Determination of Vitamin D in Milk and Infant Formula," *J. Assoc. Anal. Chem.*, 68(2)177–182, 1985;

Haroon, Y., M. J. Shearer, G. McEnery, V. E. Allan and P. Barkhan, "Assay of Vitamin K-1 (Phylloquinone) by High-Performance Liquid Chromatography: Values For Human and Cow's Milk," *Proc. Nutr. Soc.*, 39(2):49A, 1980;

Atuma, S. S. "Electrochemical Determination of Vitamin E in Margarine, Butter and Palm Oil," *J. Sci Food. Agric.*, 26(4):393–399, 1975; and Bushway, R. J. "Determination of Alpha- and Beta-Carotene in Some Raw Fruits and Vegetables by High-Performance Liquid Chromatography," *J. Agr. Food Chem.*, 34(3):409–412, 1986.

4. Calories

Calories can be viewed as a measure of a class of nutrients essential to life. Nutrients which provide the essential calories to life are fats, sugars and proteins, in their various proportions in any food mixture. Calories are also a measure of energy which can be determined by burning a single nutrient, or mixture of nutrients in a process called "complete combustion." One then measures the heat given off in the combustion process by allowing that heat to be transferred to a standard substance such as water, and measuring the temperature change of this indicator substance. Details on these procedures for measuring calories can be found in *The Handbook of Chemistry and Physics*, 1993, or in any standard physical chemistry text.

5. Percent Calories as Fat

Percent calories as fat can be determined by forming a simple ratio between the total calories due to fat present and the total calories. An inversion factor, e.g., 1 gm of fat yields 9 calories, can be used. (Cholesterol is often present in foods in such small amounts that it is not material in this calculation).

6. Protein (and Protein-Related Components)

The quantity of protein in a food can be determined by amino acid analysis. See, for example, the following references:

Iwasaski, M. and R. Harada, "Proximate and Amino Acid Composition of the Roe and Muscle of Selected Marine Species," *J. Food Sci.*, 50:1585–1587, 1985;

Jhaveri, S. N., P. A. Karakoltsidis, J. Montecalvo Jr. and S. M. Constantinides, "Chemical Composition and Protein Quality of Some Southern New England Marine Species," *J. Food Sci.*, 49:110–113, 1984 (protein, lipid, moisture, amino acids, Ca, Mg, Na, Zn, Fe, Cu, Mn, Ni, Cd);

Seet, S. T. and W. D. Brown, "Nutritional Quality of Raw, Pre-cooked and Canned Albacore Tuna (*Thunnis alalunga*)," *J. Food Sci.* 48:28.8–289, 1983. (amino acids, thiamin, riboflavin, niacin, Na, K, Ca, Fe, Cu);

Sayem-El-Daher, N., R. E. Simard and L. L'Heureux, "Determination of Mono-, Di- and Polyamines in Foods Using a Single-Column Amino Acid Auto-Analyzer," *J. Chromatogr.*, 256(2):313–321, 1983; and Zee, J. A., R. E. Simard and L. L'Heureux, "Evaluation of Analytical Methods for Determination of Biogenic Amines in Fresh and Processed Meat," *J. Food Prot.*, 46(12):1044–1049, 1054, 1983.

7. Dietary Fiber

The quantity of fiber can be determined by "bench" crude analysis as illustrated in the following references:

Lanza, E. and R. R. Butrum, "A Critical Review of Food Fiber Analysis and Data," *J. Am. Diet. Assoc.*, 86 (6):732–743, 1986;

Marlett, J. A. and J. G. Chesters, "Measuring Dietary Fiber in Human Foods," *J. Food Sci.*, 50(2):410–414, 423, 1985; and Prosky, L., N. G. Asp, I. Furda, J. W. Devries, T. F. Schweizer and B. F. Harland, "Determination of Total Dietary Fiber in Foods and Food Products: Collaborative study," *J. Assoc. Off. Anal. Chem.*, 68(4):677–679, 1985.

8. Sugars, Carbohydrates

The quantity of carbohydrate can be determined by chromatography, as illustrated in the following references:

Englyst, H. N., V. Anderson and J. H. Cummings, "Starch and Non-Starch Polysaccharides in Some Cereal Foods," *J. Sci. Food Agric.*, 34:1434–1440, 1983;

Li, B. W. and P. J. Schuhmann, "Sugar Analysis for Fruit Juices: Content and Method," *J. Food Sci.*, 48:633–634, 1983;

Li, B. W. and P. J. Schuhmann and J. M. Holden, "Determination of Sugars in Yogurt by Gas-Liquid Chromatography," *J. Agric. Food Chem.* 31(5):985–989, 1983; and Sandberg, A. S. and R. Ahderinne, "HPLC Method For Determination of Inositol Tri-, Tetra-, Penta-, and Hexaphosphates in Foods and Intestinal Contents," *J. Food Sci.*, 51(3):547–550, 1986.

B. Combining to Form Sums

As a "shortcut," rather than conducting chemical and/or physical analyses of foods each time one wants to depict contents of a food mixture, one can consult a reference work containing a compendium of such information obtained from prior analyses, such as those outlined in detail above. Compendia of nutritional data for selected foods have been published. See, for example, Jean A. T. Pennington, *Food Values*, 15th Edition, Harper & Row, New York (1989). The aforementioned new Nutritional and Labeling law specifically allows the use of such a reference in calculating the respective quantities of nutrients in foods. Of course, using such a reference just means that the aforementioned chemical and physical analyses were previously done by someone else; the step was nonetheless performed. Also, instead of calculating a sum for each nutrient in each food in a composition and totalling the sums for each nutrient in the composition, one could equivalently determine the nutrient sums directly by analyzing the composition.

If a summing approach is pursued, the process can be accomplished by hand, from values either empirically derived or obtained from extended compilations of nutritional data as described above. Alternatively, a table of basic nutrient values can be constructed within a programmed computer to do the summing. An example of a summing process from a food composition sample—namely, a recipe—is as follows:

SAMPLE RECIPE

Moroccan Spare Ribs With Couscous And Balsamic Vinegar (Can use strips of chuck roast/steak in place of ribs for health reasons, if need be—but best with ribs).

Serves 4

3 tablespoons of olive oil 2 pounds of pork back ribs, cut up 6 tablespoons of balsamic vinegar ½ cup of chicken broth (bouillon cube OK)

1 bay leaf 2 yellow bell peppers, remove seed and cut into longitudinal strips.

2 red bell peppers (do not use green peppers) cut into strips approx. 3"×½".

4 large mushrooms, sliced (optional)

4 large cloves garlic, crushed 1 teaspoon of red pepper flakes

Couscous for 4

Fresh ground pepper to taste

Heat oil in deep casserole and brown ribs well; remove and keep meat warm, then brown pepper strips lightly; if using mushrooms, add and brown lightly; remove vegetables; drain on paper towels and keep warm; return ribs and ½ of crushed garlic to pan-add 3 tablespoons of balsamic vinegar, broth, 1 bay leaf, and 1 teaspoon of red pepper flakes. Simmer over very low heat for 45 minutes, then uncover and boil away most of the broth.

Mix remaining crushed garlic with the remaining 3 tablespoons of balsamic vinegar. Return pepper strips and mushrooms briefly to pan along with vinegar/garlic composition. Heat all through thoroughly.

Serve by mounding couscous on a platter in a flat cone shape—drape ribs and peppers around the cone vertically.

| Ingredient | Amount of Ingredient | Unit Value | Calories of Total Ingredient | Protein GM | Sodium MG | Carbo GM | Choles MG | Fat GM | Fiber GM |
|---|---|---|---|---|---|---|---|---|---|
| Olive Oil | 3 T | 1 T | 119/357 | 0/0 | 0/0 | 0/0 | 0/0 | 13/39 | 0/0 |
| Pork Spare Ribs | 2# | 1/4# | 397/3200 | 30/240 | 93/744 | 0/0 | 121/968 | 30/240 | 0/0 |
| Vinegar | 6 T | 1 T | 0/0 | 0/0 | 0/0 | 0.4/2.4 | 0/0 | 0/0 | 0/0 |
| Chicken Broth | 1/2 c | c | 19/9 | 2.4/1.2 | 99/50 | 1.1/0.5 | 0/0 | 0.6/0.3 | 0/0 |
| Fresh Garlic | 4 | Cloves | 13/52 | 0.6/2.4 | 1/4 | 1.0/4.0 | 0/0 | 0.1/0.4 | 0/0 |
| Bell Peppers | 4 | Each | 12/48 | 0.4/1.6 | 2/8 | 2.7/10.8 | 0/0 | 0.2/0.8 | 0.6/2.4 |
| Couscous | 3 c | 1 c. Cooked | 159/480 | 5.2/15.6 | 1/3 | 344/102 | 0/0 | 0.7/2.1 | 0.6/2.4 |
| TOTAL | | | 4146 | 260 | 808 | 120 | 968 | 282.3 | 1.26 |
| (Divided into 4 Servings) | | | 1036 | 65 | 202 | 30 | 242 | 70 | .41 |

SAMPLE TABULATION FOR MOROCCAN SPARERIBS RECIPE

Percent Calories as Fat = 62%

In the above-given sample tabulation," "#" represents "pounds," "T" represents "tablespoon," "c" represents "cup," "MG" represents "milligrams," and "GM" represents "grams."

C. Defining Pictorial Images

Figure 2:
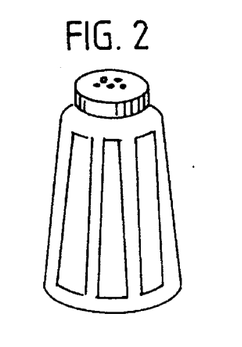
FIG. 2 is a representative symbolic nutrient label for sodium.

In constructing pictorial images to symbolically convey the nutritional information, there are many suitable possibilities. Preferably, each image is selected to suggest a specific nutrient. For example, a salt shaker is suggestive of sodium (i,e., salt), as illustrated in FIG. 2. A different symbol can be defined for each such nutrient. But to avoid overwhelming consumers with symbols, it may be better to have symbols for only some nutrients. For example, restricting the symbols to those nutrients that are either essential or harmful to health—such as those identified by law. Representative symbols are shown in FIGS. 2 through 8.

A pictorial image can represent a nutritional standard, such as the amount of the nutrient for daily human consumption. One way to standardize the images is to have the outline of each image form an area corresponding to the standard. That is, the area within the border of the image represents 100% of the allowed or recommended daily amount of the nutrient. The fraction of the allotment provided by a specific food or food composition can be illustrated in the context of the image—for example, by shading in a corresponding portion of the area within the border of the symbol, as illustrated in FIG. 3. (Alternatively, height can be used to compare the standard with the amount in a food composition.)

Pictorial images can be chosen to represent standards set by law for labeling nutrients, and/or to represent other information about the food. Details regarding the illustrative symbols preferred herein are provided below.

1. Sodium

FIG. 2 shows a pictorial image of a salt shaker. The image is defined to suggest salt, which in turn suggests sodium. The image has an outline representative of a standard: the 2400 mg. total sodium allowance recommended per day in the Nutrition and Labeling Law. The height to which the shaker is filled represents the relative proportion of the 2400 mg present—e.g., 1200 mg=½ the height, 800 mg=⅓ the height, etc.

2. Cholesterol

FIG. 3 shows a pictorial image of a heart, which is suggestive of cholesterol. The heart has an outline, and a portion of the area within the heart is black. The black area represents the portion of the daily allotment of cholesterol that would be ingested from eating a particular composition of food.

3. Fat

Figure 4:
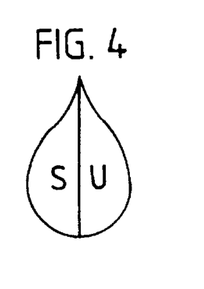
FIG. 4 is a representative symbolic nutrient display label for fat (and can be vertically divided as indicated, to simultaneously display two kinds of fat).
Figure 5:
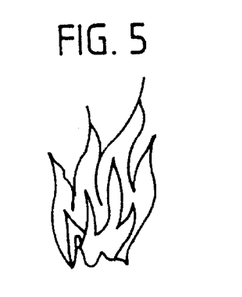
FIG. 5 is a representative symbolic nutrient label for calories.

FIG. 4 shows an "oil drop," which can be used to represent all fats. The oil drop is divided into a portion marked "S" and another portion marked "U" to respectively represent proportions of the fat present as saturated and unsaturated fat.

4. Calories

A calorie is a quantity of heat, which is suggested by an image of fire. See, for example, FIG. 5. While the larger fire in FIG. 5 could be crosshatched or otherwise filled in to show a portion of the standard; alternatively, a second smaller fire can be used to represent a portion of the larger fire.

5. Percent Calories as Fat

A key nutrient which has been the subject of considerable abuse in labeling claims in the past is fat. For fat, there is an additional pictorial image representing the percent of calories as fat. The percent of calories as fat is a better indicator than the percent of fat simpliciter, because the former figure cannot be manipulated to mislead the consumer concerning the fat content of a food.

Figure 6:
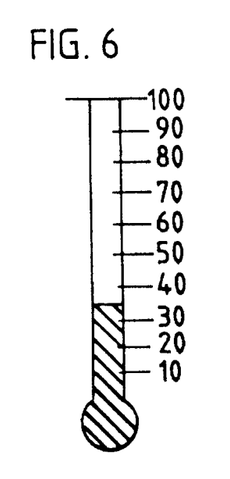
FIG. 6 is a representative symbolic nutrient label for percent of calories as fat.

FIG. 6 shows the percent of calories as fat by means of the elevation of a thermometer calibrated to show a percentile. Fats are a complicated category, as notions such as "saturated," "unsaturated," and "cholesterol" might all be represented. Cholesterol is present in most foods in such a negligible weight amount that it does not significantly contribute to the overall data about fats indicated in grams. But the importance of cholesterol with respect to heart disease gives reason to have a separated symbol ♥, to indicate the daily allowance which is presently 300 mg. The law requires a statement of the percent of calories as fat in a food composition, and many recent diet plans are based on this percentage. This information can thus be communicated by a symbolic representation.

6. Protein

Figure 7:
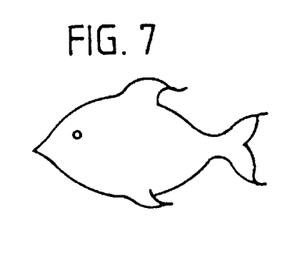
FIG. 7 is a representative symbolic nutrient label for protein.

FIG. 7 is a fish, which may suggest protein. Note that the particular fish depicted is not important. The notion of protein might equally be suggested by an image of a cow. What is important, though, is to illustrate the standard by using an image easily associated with the nutrient or concept that it represents.

7. Carbohydrates

Figure 8:
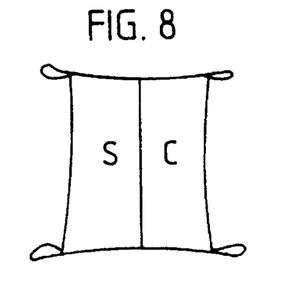
FIG. 8 is a representative symbolic nutrient label for carbohydrates.

In FIG. 8, a sack of sugar can be used to suggest carbohydrates. Carbohydrates come in two kinds—simple, such as sugars found in syrups, etc., and complex, such as the carbohydrates found in bread, pastas and cereals. Present thinking is that it is preferable to eat a minimum of simple carbohydrates, but a maximum amount of complex carbohydrates. Thus, the symbol for carbohydrates can be divided into two compartments to allow the symbol to show relative proportions of simple (the "S" portion of the sack) and complex (the "C" portion of the sack) carbohydrates.

8. Fiber

Figure 9:
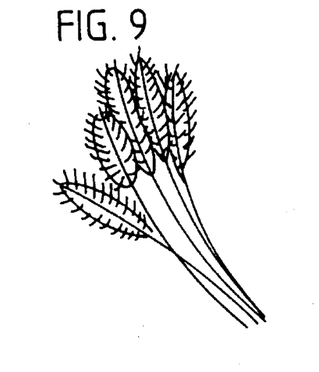
FIG. 9 is a representative symbolic nutrient label for fiber.

FIG. 9 shows stalks of wheat, which is suggestive of fiber. Fiber is widely considered advantageous in a human diet. Thus, the pictorial image may show, say, 3 stalks of wheat (with each stalk representing 10 grams of dietary fiber). The three filled-in stalks indicate that a food meets the daily suggested amount of fiber. Additional stalks indicate that the particular food composition exceeds a daily recommended minimum amount.

D. Combining the Sum with the Image

An amount of a nutrient or calories associated with a food mixture is then illustrated in the context of the standard. For example, a total sum for cholesterol is illustrated in the context of the heart image of FIG. 3 as an area partially filling the heart image. This manner of combining can be a shading in the corresponding portion of the image, or the portion can be raised, lowered, or textured to permit sensing by visually impaired individuals.

E. Combining Images

Individual images defined in accordance with the present invention can be presented in a series of images. The individual image or series of images can be printed to form labeling for produce bins, meat counters, cans, boxes, frozen food containers, and/or even for recipes and restaurant menu items.

Images can represent any feature or features desired regarding a food. These labels may contain, in addition, the new federally defined concepts of "free," "low," "high" "source of," "reduced in," "low in," "light," "light in," etc. as printed matter, along with federally defined recommended amounts of nutrients in specified calorie diets.

F. Manufacturing/Printing a Label

Printing processes suitable for the present invention can be classified into four broad families: relief, intaglio, planographic, and porous. To be printed to form a label by any of these processes, the pictorial image is transferred by means of a carrier such as photopolymer plates, rubber plates, gravure cylinders, offset plates, silk screens, etc.

1. Relief Printing

With respect to relief printing, the printing areas of the image carrier are raised above the plane of the supporting material, for example, as in a print made from raised areas on a block of wood. Modern techniques for making relief printing include letterpress, newspaper relief, flexography, and dry offset printing. The design to be printed stands at a uniform height above the non-printing areas so that only the raised area receives ink from the inking rollers that pass lightly over its face.

As to letterpress printing, the images (or type) areas are raised above the non-printing areas in a mirror image of the pictorial image desired. The ink rollers touch only the top surface of the images to be printed. The inked image is then transferred directly to the paper, which reverses the mirror image. Letterpress can also be used to emboss the pictorial image and/or the area within the image to produce a tactile effect which can be sensed by visually impaired customers.

Newspaper Relief Printing, as the name implies, is a printing method developed for high speed, efficient production for the printing of newspapers. The printing image carriers are usually curved stereotype plates cast in type metal. The paper stock is inexpensive, uncoated, and made primarily of groundwood. Newsprint ink is also inexpensive and does not form a dry ink film like other letterpress ink. Instead, it dries by absorption of the ink vehicle. It is another way to produce the images according to the invention.

Flexography is a relief printing method using flexible rubber or photopolymer plates and fast-drying solvent or water-based inks. It is used primarily on rotary web presses. The image is usually printed on one side of the web, using very little pressure. The quality of the flexography has improved in recent years, making the process suitable for printing labeling according to the present invention.

Dry offset is also known as indirect relief offset and letterset. A thin, shallow-etched metal plate of Dycril or a photopolymer plate, like a Letterflex or Nyloprint plate, can be used to print one or more pictorial images, particularly for extremely long run custom orders.

2. Intaglio

The printing plates for gravure or intaglio printing have the pictorial image etched below the surface, forming an array of microscopic cups which differ in depth and diameter. The ink used for this process is much more fluid than letterpress inks, and flows into the tiny cups when ink is rolled over the plate. The surface of the plate, which is non-printing, is wiped clean of ink before the paper is brought into contact with it. When paper contacts the printing plate, the ink cups dump their contents; the large cups produce dark tones and the small cups product light tones. This printing process produces the greatest fidelity in practicing the present invention because of the ability to lay down different thicknesses of ink.

3. Planographic

As the name implies, the printing and non-printing areas are in the same plane on the image carrier. The printing area is chemically sensitized, so that it will attract lithographic inks. The non-printing areas are treated so that they will not accept ink. Most planographic printing methods are based on the principle that oil and water do not mix. Lithographic inks are oil-based, and most lithographic presses use a water-solution dampening system. Offset lithography, direct lithography, and collotype are the most common planographic printing methods. Each can be used to carry out the present invention.

4. Porous Printing

Screen printing (also known as silk screen printing) is the most common porous printing method. The image is formed by pressing a highly viscous printing ink or paint through a mesh screen. Non-image areas are formed by blocking selected areas of the screen with a stencil.

The definition and resolution characteristics of screen-printed pictorial images have a characteristic "thick film" ink layer which can usually be felt with the fingertips. This approach is therefore suitable for producing pictorial images, and areas therein, detectable by touch. Also, in this and the other printing techniques discussed herein, a printed texture can be created by adding a component to the ink or paint—such as a resin, as used particularly in thermography.

5. Non-Impact Printing

In addition to the printing processes listed above, there are several other printing processes that, although not presently preferred, could be used. These include the thermal, electrographic, electrostatic, photoelectrostatic and ink jet printing.

6. Summary

Any of the foregoing printing processes are suitable for printing a label having both said pictorial image and area to form a pictorial comparison of the quantity of the nutrient in the composition with the standard (recommended/allowed) amount of the nutrient. The advantages and disadvantages of a given printing processes will depend on the specific application of the present invention.

While the invention herein has been disclosed with respect to the best mode and embodiment known to the inventor, it should be understood that teaching of the invention is illustrative. The scope of invention reaches other versions, embodiments, and applications—along with their equivalents—as defined in the following claims.

I claim:

1. A process for analyzing nutritional content of a composition of food to produce a calculated printed representation of the nutritional content in comparison to a quantitative standard, the process comprising the steps of:

determining a total amount of a nutrient in a composition of food;

calculating a first area representing said total amount of the nutrient in the composition and calculating a second area representing a quantitative standard for daily human consumption of the nutrient, wherein the second area is confined to a region within a pictorial image shape representing the nutrient and wherein said first area is proportionate to said second area, thereby forming a ration represented by the areas; and printing said pictorial image shape and said first area to form a pictorial display of the ratio represented by the first and second areas to illustrate a comparison of the total amount of the nutrient in the composition with the quantitative standard.

2. The process of claim 1, wherein the step of printing comprises producing the pictorial image shape and the first area so that each is detectable by touch for sensing by a visually impaired person.

3. The process of claim 2, wherein the step of printing the pictorial image shape and the first area includes embossing.

4. The process of claim 2, wherein the step of printing the pictorial image shape and the first area includes printing with a medium from the group consisting of textured ink and paint.

5. The process of claim 1, wherein the nutrients are from a group consisting of: sodium, cholesterol, protein, carbohydrates, fiber, and fat.

6. The process of claim 1, wherein:

the nutrient is fat; and wherein the step of determining includes finding respective total quantities of saturated fat and unsaturated fat in the composition; and further comprising the steps of:

calculating an area representing said total quantity of saturated fat and calculating an area representing said total quantity of unsaturated fat, the areas representing the quantities of saturated fat and unsaturated fat cumulatively being confined to a region defined by a second pictorial image shape, thereby forming a ratio of the quantities of saturated fat and unsaturated fat as represented by the areas; and wherein the step of printing includes printing said second pictorial image shape and said areas representing the quantities of saturated fat and unsaturated fat to form a pictorial display of the ratio of areas representing the quantities of saturated fat and unsaturated fat represented by the areas to illustrate a comparison of the respective total quantities of saturated fat and unsaturated fat in the composition.

7. The process of claim 1, further comprising the steps of:

finding a total amount of a second nutrient in the composition;

calculating a first area representing said total amount of the second nutrient in the composition and calculating a second area representing a quantitative standard for daily human consumption of the second nutrient, wherein the second area is confined to a region defined by a second pictorial image shape representing the second nutrient and wherein said first area for the second nutrient is proportionate to said second area for the second nutrient, thereby forming a second ratio represented by the first area for the second nutrient and the second area for the second nutrient; and printing said second pictorial image shape and said first area for the second nutrient to form a pictorial display of the second ratio to illustrate a comparison of the total amount of the second nutrient in the composition with the second quantitative standard and to further illustrate a comparison of the pictorial displays.

8. The process of claim 1, wherein further comprising the steps of:

finding a total amount of each of a plurality of nutrients in the composition;

for each of said plurality of nutrients, calculating a first area representing said respective total amount of the respective nutrient in the composition and calculating a second area representing a quantitative standard for daily human consumption of the respective nutrient, wherein the second area for the respective nutrient is confined to a respective region defined by a respective pictorial image shape representing the respective nutrient and wherein said first area for the respective nutrient is proportionate to said second area for the respective nutrient, thereby forming a respective ratio represented by the first area for the respective nutrient and the second area for the respective nutrient; and printing said respective pictorial image shapes and said respective areas for the respective nutrients to form respective pictorial displays of the respective ratios represented by the respective areas for the respective nutrients to illustrate a comparison of the total amount of the respective nutrients in the composition with the respective quantitative standards and to further illustrate a comparison of the pictorial displays.

9. The process in any one of claims 1–4 or 7–8, further comprising the steps of:

finding a total number of calories in the composition and a total number of calories present as fat in the composition;

calculating a first area representing said total number of calories present in the composition and calculating a second area representing said total number of calories present in the composition as fat, both said first area representing said total number of calories present in the composition and said second area representing said total number of calories present in the composition as fat being confined to a pictorial image shape and wherein said second area representing said total number of calories present in the composition as fat is proportionate to said first area representing said total number of calories present in the composition, thereby forming a ratio represented by said first area representing said total number of calories present in the composition and said second area representing said total number of calories present in the composition as fat; and printing said pictorial image and said first area representing said total number of calories present in the composition and said second area representing said total number of calories present in the composition as fat to form a pictorial display of the ratio represented by said first area representing said total number of calories present in the composition and said second area representing said total number of calories present in the composition as fat to illustrate a comparison of said first area representing said total number of calories present in the composition and said second area representing said total number of calories present in the composition as fat.

* * * * *